(12) United States Patent
Hercouet et al.

(10) Patent No.: US 9,987,205 B2
(45) Date of Patent: *Jun. 5, 2018

(54) OIL-RICH COMPOSITION AND USE THEREOF IN A LIGHTENING OR NON-LIGHTENING DIRECT DYEING PROCESS

(71) Applicant: L'OREAL, Paris (FR)

(72) Inventors: Leila Hercouet, Neuilly Plaisance (FR); Marie Cognet, Charbonnieres (FR)

(73) Assignee: L'OREAL, Paris ( * ) Notice: Subject to any disclaimer, the term of this patent is extended or adjusted under 35 U.S.C. 154(b) by 0 days. days.

This patent is subject to a terminal disclaimer.

(21) Appl. No.: 14/437,958

(22) PCT Filed: Oct. 28, 2013

(86) PCT No.: PCT/EP2013/072515
§ 371 (c)(1),
(2) Date: Apr. 23, 2015

(87) PCT Pub. No.: WO2014/067901
PCT Pub. Date: May 8, 2014

(65) Prior Publication Data
US 2015/0272842 A1    Oct. 1, 2015

(30) Foreign Application Priority Data

Oct. 31, 2012   (FR) ..................... 12 60424

(51) Int. Cl.
| | | |
|---|---|---|
| *A61Q 5/10* | (2006.01) | |
| *A61K 8/31* | (2006.01) | |
| *A61K 8/34* | (2006.01) | |
| *A61K 8/39* | (2006.01) | |
| *A61K 8/60* | (2006.01) | |
| *A61Q 5/06* | (2006.01) | |
| *A45D 34/00* | (2006.01) | |
| *A61K 8/41* | (2006.01) | |
| *A61K 8/49* | (2006.01) | |

(52) U.S. Cl.
CPC ............... *A61K 8/31* (2013.01); *A45D 34/00* (2013.01); *A61K 8/342* (2013.01); *A61K 8/39* (2013.01); *A61K 8/41* (2013.01); *A61K 8/498* (2013.01); *A61K 8/604* (2013.01); *A61Q 5/065* (2013.01); *A61K 2800/432* (2013.01); *A61K 2800/4322* (2013.01); *A61K 2800/4324* (2013.01); *A61K 2800/592* (2013.01); *A61K 2800/87* (2013.01); *A61K 2800/88* (2013.01); *A61K 2800/882* (2013.01)

(58) Field of Classification Search
CPC . A61K 8/41; A61K 8/39; A61K 8/604; A61K 8/498; A61K 8/342; A61K 8/31; A61K 2800/4324; A61K 2800/4322; A61K 2800/432; A61K 2800/88; A61K 2800/882; A61K 2800/87; A61K 2800/592; A45D 34/00
USPC ............................................................ 8/405
See application file for complete search history.

(56) References Cited

U.S. PATENT DOCUMENTS

| | | |
|---|---|---|
| 3,869,454 A | 3/1975 | Lang et al. |
| 3,985,499 A | 10/1976 | Lang et al. |
| 4,025,301 A | 5/1977 | Lang |
| 4,151,162 A | 4/1979 | Lang et al. |
| 5,708,151 A | 1/1998 | Mockli |
| 7,311,736 B2 | 12/2007 | Burgaud et al. |
| 7,399,320 B2 | 7/2008 | Burgaud et al. |
| 2005/0028300 A1 | 2/2005 | Burgaud et al. |
| 2006/0070191 A1 * | 4/2006 | Lang ................. A61K 8/49 8/406 |
| 2006/0156479 A1 | 7/2006 | Hercouet et al. |
| 2008/0092307 A1 | 4/2008 | Burgaud et al. |

(Continued)

FOREIGN PATENT DOCUMENTS

| | | |
|---|---|---|
| EP | 0714954 A2 | 6/1996 |
| EP | 1378544 A2 | 1/2004 |

(Continued)

OTHER PUBLICATIONS

International Search Report and Written Opinion for PCT/EP2013/072515, dated Jun. 11, 2014.

(Continued)

*Primary Examiner* — Eisa B Elhilo

(74) *Attorney, Agent, or Firm* — The Marbury Law Group, PLLC

(57) ABSTRACT

The present invention relates especially to a composition for dyeing keratin fibers, in particular human keratin fibers such as the hair, comprising: (i) one or more fatty substances in a content ranging from 40% to 85% by weight relative to the total weight of the dye composition, (ii) one or more oxyethylenated fatty alcohols with an oxyethylene number of less than or equal to 10, and (iii) one or more nonionic surfactants of alkylpolyglucoside type, (iv) optionally one or more alkaline agents, (v) one or more direct dyes which are preferably cationic, anionic or neutral. The present invention also relates to a process for dyeing keratin fibers, comprising the application to the said fibers of an above mentioned composition, optionally in the presence of a composition comprising one or more chemical oxidizing agents; the dye composition possibly resulting from the mixing of several compositions. Finally, the invention relates to devices that are suitable for performing this process.

15 Claims, No Drawings

(56) References Cited

U.S. PATENT DOCUMENTS

2010/0158844 A1\* 6/2010 Braida-Valerio ........ A61K 8/22
                                                            424/70.1
2014/0068876 A1   3/2014 Rapold et al.

FOREIGN PATENT DOCUMENTS

| EP | 1674073 A1 | 6/2006 |
| FR | 2140205 A1 | 1/1973 |
| FR | 2189006 A1 | 1/1974 |
| FR | 2285851 A1 | 4/1976 |
| FR | 2970176 A1 | 7/2012 |
| WO | 95/01772 A1 | 1/1995 |
| WO | 95/15144 A1 | 6/1995 |
| WO | WO 2012/095394 A2 \* | 7/2012 ............... A61Q 5/10 |

OTHER PUBLICATIONS

Todd, Charles, et al., "Volatile Silicone Fluids for Cosmetic Formulations," Cosmetics and Toiletries, vol. 91, Jan. 1976, pp. 29-32.

\* cited by examiner

OIL-RICH COMPOSITION AND USE THEREOF IN A LIGHTENING OR NON-LIGHTENING DIRECT DYEING PROCESS

This is a national stage application of PCT/EP2013/072515, filed internationally on Oct. 28, 2013, which claims priority to U.S. Provisional Application No. 61/732,923, filed on Dec. 3, 2012; as well as French Application 1260424, filed on Oct. 31, 2012.

The present invention relates to a dye composition comprising one or more fatty substances, one or more oxyethylenated fatty alcohols with an oxyethylene number of less than or equal to 10 and one or more surfactants of alkylpolyglucoside type and one or more direct dyes.

The present invention relates to the field of the direct dyeing of human keratin fibres, and in particular the hair, under lightening or non-lightening conditions, in other words performed, respectively, with or without chemical oxidizing agent(s).

Two major methods for dyeing human keratin fibres, and in particular the hair, are known.

The first, known as oxidation dyeing or permanent dyeing, consists in using one or more oxidation dye precursors, more particularly one or more oxidation bases optionally combined with one or more couplers. These compounds are used in the presence of a chemical oxidizing agent, generally hydrogen peroxide, and an alkaline agent, in order to bring about oxidative condensation of the precursors (base/coupler) within the fibre.

The second dyeing method, which is the subject of the invention, known as direct dyeing or semi-permanent dyeing, comprises the application of direct dyes, which are molecules with affinity for the fibres and which colour even in the absence of an oxidizing agent added to the compositions containing them. Given the nature of the molecules used, they tend rather to remain on the surface of the fibre and penetrate relatively little into the fibre, when compared with the small molecules of oxidation dye precursors.

The direct dyes generally used are chosen from nitrobenzene, anthraquinone, nitropyridine, azo, methine, azomethine, xanthene, acridine, azine and triarylmethane direct dyes. The chemical species used may be nonionic, anionic (acidic dyes) or cationic (basic dyes). Direct dyes may also be natural dyes.

Compositions containing one or more direct dyes are applied to keratin fibres for a time necessary to obtain the desired coloration, and are then rinsed out.

However, the colorations resulting therefrom are said to be temporary or semi-permanent. Specifically, the dyes are desorbed from the surface or from a region close to the surface of the fibre more or less readily, resulting in an appreciable reduction in the staying power over time of the coloration. Problems of build-up of the dye may also arise.

The aim of the present invention is to provide novel compositions for the direct dyeing, under lightening or non-lightening conditions, of human hair, which make it possible to improve the build-up of the dyes.

Thus, one subject of the present invention is a composition for dyeing keratin fibres, in particular human keratin fibres such as the hair, comprising:
(i) one or more fatty substances in a content ranging from 40% to 85% by weight relative to the total weight of the dye composition,
(ii) one or more oxyethylenated fatty alcohols with an oxyethylene number of less than or equal to 10, and
(iii) one or more nonionic surfactants of alkylpolyglucoside type,
(iv) optionally at least one alkaline agent,
(v) one or more direct dyes.

A subject of the present invention is also a process for dyeing keratin fibres, in particular human keratin fibres such as the hair, comprising the application to the said fibres of a cosmetic composition as defined above in the presence or absence of one or more chemical oxidizing agents.

The dye composition may result from the extemporaneous mixing, before application, of several compositions.

The invention also relates to a multi-compartment device using a first compartment containing the dye composition as defined above, and a second compartment containing one or more chemical oxidizing agents.

The invention also relates to a multi-compartment device comprising:
a first compartment containing a composition (A) comprising at least one fatty substance (i), at least one oxyethylenated fatty alcohol with an oxyethylene number of less than or equal to 10 (ii), at least one nonionic surfactant of alkylpolyglucoside type (iii), optionally at least one direct dye (v), optionally at least one alkaline agent (iv),
a second compartment containing a composition (B) containing at least one direct dye (v) and/or at least one alkaline agent (iv),
the mixing of the first and second compartments resulting in a composition according to the invention, and preferably comprising at least one alkaline agent,
optionally a third compartment containing an oxidizing composition (C) comprising one or more chemical oxidizing agents.

The term "chemical oxidizing agent" means any chemical oxidizing agent other than atmospheric oxygen.

Other characteristics, aspects, subjects and advantages of the present invention will emerge even more clearly on reading the description and the examples that follow.

In the text hereinbelow, and unless otherwise indicated, the limits of a range of values are included in that range.

For the purposes of the present invention, the term "build-up" of the colour of keratin fibres means the variation in coloration between locks of undyed grey hair and locks of dyed hair.

The expression "at least one" is equivalent to the expression "one or more".

Fatty Substance:

As indicated previously, the dye composition according to the invention comprises one or more fatty substances (i).

The term "fatty substance" means an organic compound that is insoluble in water at ordinary temperature (25° C.) and at atmospheric pressure ($1.013 \times 10^5$ Pa; 760 mmHg) (solubility of less than 5%, preferably 1% and even more preferentially 0.1%). They have in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The fatty substances of the invention do not contain salified carboxylic acid groups. In addition, the fatty substances of the invention are not (poly)oxyalkylenated (especially $C_2$-$C_3$) or (poly)glycerolated ethers.

The term "oil" means a "fatty substance" that is liquid at room temperature (25° C.) and at atmospheric pressure ($1.013\times10^5$ Pa; 760 mmHg).

The term "non-silicone oil" means an oil not containing any silicon atoms (Si) and the term "silicone oil" means an oil containing at least one silicon atom.

More particularly, the fatty substances are chosen from $C_6$-$C_{16}$ alkanes, hydrocarbons containing more than 16 carbon atoms, non-silicone oils of animal origin, plant oils of triglyceride type, synthetic triglycerides, fluoro oils, fatty alcohols, fatty acid and/or fatty alcohol esters other than triglycerides and plant waxes, non-silicone waxes and silicones, and mixtures thereof.

It is recalled that the fatty alcohols, esters and acids more particularly have at least one linear or branched, saturated or unsaturated hydrocarbon-based group comprising 6 to 30 and better still from 8 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes. Mention may be made, by way of example, of hexane, dodecane or isoparaffins, such as isohexadecane or isodecane.

As hydrocarbon-based oils (hydrocarbons containing more than 16 carbon atoms) of animal or plant origin, mention may be made of perhydrosqualenes, for example including olive squalane.

The triglyceride oils of plant or synthetic origin are preferably chosen from liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

The linear or branched hydrocarbons of mineral or synthetic origin having more than 16 carbon atoms are preferably chosen from liquid paraffins, petroleum jelly, liquid petroleum jelly, polydecenes or hydrogenated polyisobutene, such as Parleam®.

As regards the $C_6$-$C_{16}$ alkanes, they are linear, branched or optionally cyclic. By way of example, mention may be made of hexane, dodecane and isoparaffins such as isohexadecane and isodecane.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols which are suitable for the implementation of the invention are more particularly chosen from saturated or unsaturated and linear or branched alcohols comprising from 6 to 30 carbon atoms and preferably from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecyl-pentadecanol, oleyl alcohol and linoleyl alcohol.

As regards the fatty acid and/or fatty alcohol esters, which are advantageously different from the triglycerides mentioned above, mention may be made in particular of esters of saturated or unsaturated and linear or branched $C_1$-$C_{26}$ aliphatic monoacids or polyacids and of saturated or unsaturated and linear or branched $C_1$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, use is preferably made of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" is understood to mean oxygen-containing hydrocarbon-based compounds that contain several alcohol functions, with or without aldehyde or ketone functions, and that comprise at least 4 carbon atoms. These sugars may be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates, arachidonates or mixtures thereof, such as, in particular, oleate/palmitate, oleate/stearate or palmitate/stearate mixed esters.

More particularly, use is made of monoesters and diesters and in particular mono- or di-oleate, -stearate, -behenate, -oleopalmitate, -linoleate, -linolenate or -oleostearate of sucrose, of glucose or of methylglucose.

An example that may be mentioned is the product sold under the name Glucate® DO by the company Amerchol, which is a methylglucose dioleate.

Examples of esters or mixtures of esters of sugar and of fatty acid that may also be mentioned include:

the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% diester-triester-polyester;

the sucrose mono-dipalmitate/stearate sold by the company Goldschmidt under the name Tegosoft® PSE.

The non-silicone wax(es) are chosen in particular from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by the company Bertin (France), or animal waxes, such as beeswaxes or modified beeswaxes (cerabellina); other waxes or waxy starting materials that may be used according to the invention are in particular marine waxes, such as that sold by the company Sophim under the reference M82, polyethylene waxes or polyolefin waxes in general.

The silicones that may be used in the dye composition according to the present invention are volatile or non-volatile, cyclic, linear or branched silicones, which are unmodified or modified by organic groups, having a viscosity from $5 \times 10^{-6}$ to 2.5 $m^2/s$ at 25° C., and preferably $1 \times 10^{-5}$ to 1 $m^2/s$.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from amino groups and alkoxy groups.

Organopolysiloxanes are defined in greater detail in Walter Noll's "Chemistry and Technology of Silicones" (1968), Academic Press. They may be volatile or non-volatile.

When they are volatile, the silicones are more particularly chosen from those having a boiling point of between 60° C. and 260° C., and more particularly still from:

(i) cyclic polydialkylsiloxanes comprising from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

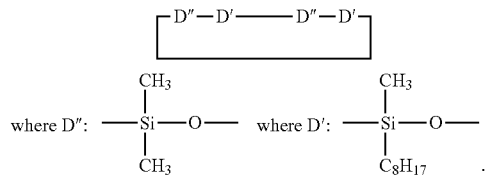

Mention may also be made of mixtures of cyclic polydialkylsiloxanes with organic compounds derived from silicon, such as the mixture of octamethylcyclotetrasiloxane and tetra(trimethylsilyl)pentaerythritol (50/50) and the mixture of octamethylcyclotetrasiloxane and oxy-1,1'-bis(2,2,2', 2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ $m^2/s$ at 25° C. An example is decamethyltetrasiloxane sold in particular under the name SH 200 by the company Toray Silicone. Silicones falling within this category are also described in the article published in Cosmetics and Toiletries, Vol. 91, January 76, pp. 27-32, Todd & Byers, *Volatile Silicone Fluids for Cosmetics*.

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to Standard ASTM 445 Appendix C.

Mention may be made, among these polydialkylsiloxanes, without limitation, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 $mm^2/s$;

the Viscasil® oils from General Electric and certain oils of the SF series (SF 96, SF 18) from General Electric.

Mention may also be made of polydimethylsiloxanes having dimethylsilanol end groups known as dimethiconol (CTFA), such as the oils in the 48 series from Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that may be used in accordance with the invention are in particular polydialkylsiloxanes and preferably polydimethylsiloxanes with high number-average molecular weights of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:
- the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by the company Dow Corning;
- the mixtures of a polydimethylsiloxane gum and of a cyclic silicone, such as the product SF 1214 Silicone Fluid from the company General Electric; this product is a gum SF 30 corresponding to a dimethicone, having a number-average molecular weight of 500 000, dissolved in the oil SF 1202 Silicone Fluid corresponding to decamethylcyclopentasiloxane;
- mixtures of two PDMSs with different viscosities, and more particularly of a PDMS gum and a PDMS oil, such as the product SF 1236 from the company General Electric. The product SF 1236 is a mixture of a gum SE 30 defined above with a viscosity of 20 m$^2$/s and of an oil SF 96 with a viscosity of 5×10–6 m$^2$/s. This product preferably comprises 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$ in which R represents an alkyl containing 1 to 16 carbon atoms. Among these products, those that are particularly preferred are those in which R denotes a $C_1$-$C_4$ lower alkyl group, more particularly methyl.

Mention may be made, among these resins, of the product sold under the name Dow Corning 593 or those sold under the names Silicone Fluid SS 4230 and SS 4267 by the company General Electric, which are silicones of dimethyl/trimethylsiloxane structure.

Mention may also be made of the resins of the trimethylsiloxysilicate type, sold in particular under the names X22-4914, X21-5034 and X21-5037 by the company Shin-Etsu.

The organomodified silicones that may be used in accordance with the invention are silicones as defined above and comprising in their structure one or more organofunctional groups attached via a hydrocarbon-based group.

Besides the silicones described above, the organomodified silicones may be polydiarylsiloxanes, especially polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from 1×10$^{-5}$ to 5×10$^{-2}$ m$^2$/s at 25° C.

Among these polyalkylarylsiloxanes, examples that may be mentioned include the products sold under the following names:
- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Mention may be made, among the organomodified silicones, of polyorganosiloxanes comprising:
- substituted or unsubstituted amino groups, such as the products sold under the name GP 4 Silicone Fluid and GP 7100 by the company Genesee or the products sold under the names Q2 8220 and Dow Corning 929 or 939 by the company Dow Corning. The substituted amino groups are in particular C1-C4 aminoalkyl groups;
- alkoxylated groups, such as the product sold under the name Silicone Copolymer F-755 by SWS Silicones, and Abil Wax® 2428, 2434 and 2440 by the company Goldschmidt.

More particularly, the fatty substances are chosen from compounds that are liquid or pasty at room temperature (25° C.) and at atmospheric pressure.

Preferably, the fatty substance is a compound that is liquid at a temperature of 25° C. and at atmospheric pressure.

The fatty substances are advantageously chosen from $C_6$-$C_{16}$ alkanes, hydrocarbons containing more than 16 carbon atoms, plant oils of triglyceride type, synthetic triglycerides, fatty alcohols, fatty acid and/or fatty alcohol esters, non-silicone waxes and silicones, or mixtures thereof.

Preferably, the fatty substance is chosen from liquid petroleum jelly, $C_6$-$C_{16}$ alkanes, polydecenes, liquid fatty acid and/or fatty alcohol esters, liquid fatty alcohols, or mixtures thereof.

More preferentially, the fatty substances are chosen from liquid petroleum jelly, $C_6$-$C_{16}$ alkanes, polydecenes and liquid fatty alcohols such as 2-octyldodecanol, oleyl alcohol or isostearyl alcohol, and liquid fatty acid and/or fatty alcohol esters, or mixtures thereof.

In particular, the fatty substance preferably present in the cosmetic composition is liquid petroleum jelly or 2-octyldodecanol. According to a preferred embodiment, the fatty substance present in the cosmetic composition is liquid petroleum jelly.

As indicated previously, the fatty substances are present in the dye composition according to the invention in a content ranging from 40% to 85% by weight, preferably from 50% to 85% by weight and better still from 60% to 85% by weight relative to the weight of the dye composition.

Preferably, these contents are indicated for compositions free of chemical oxidizing agent(s).

Fatty Alcohols Containing not More than 10 Oxyethylene Units:

The cosmetic composition according to the present invention also comprises one or more oxyethylenated fatty alcohols with an oxyethylene number of less than or equal to 10 (ii).

For the purposes of the present invention, the term "oxyethylenated fatty alcohol" means an oxyethylenated alcohol with a hydrocarbon-based chain comprising at least 6 carbon atoms.

According to the invention, the term "oxyethylenated fatty alcohol" means any fatty alcohol having the following structure:

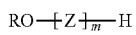

in which:

R denotes a saturated or unsaturated, linear or branched radical comprising from 6 to 40, in particular from 8 to 30, preferably less than 16 and better still from 10 to 15 carbon atoms and Z represents an oxyethylene radical of formula (I) below:

$$-CH_2-CH_2-O- \quad (I)$$

m represents the number of ethylene oxide groups less than or equal to 10, preferably ranging from 2 to 10.

Oxyethylenated fatty alcohols (ii) that are particularly preferred according to the invention are saturated or unsaturated linear fatty alcohols comprising from 10 to 20 carbon atoms, especially 12 carbon atoms, and from 2 to 8 ethylene oxide groups and better still from 2 to 5 ethylene oxide groups, in particular two ethylene oxide groups.

As compounds of oxyalkylenated fatty alcohol type, mention may be made especially of the following commercial products:

Mergital LM2 (Cognis) [lauryl alcohol 2 OE];

Empilan KA 2.5/90FL (Albright & Wilson) and Mergital BL309 (Cognis) [decyl alcohol 3 OE];

Empilan KA 5/90FL (Albright & Wilson) and Mergital BL589 (Cognis) [decyl alcohol 5 OE];

Emulgin 05 (Cognis) [oleocetyl alcohol 5 OE].

Preferably, the oxyethylenated fatty alcohol (ii) present in the cosmetic composition according to the invention is lauryl alcohol comprising two ethylene oxide groups.

The oxyethylenated fatty alcohol(s) with an ethylene oxide number of less than or equal to 10 (ii) may be present in the cosmetic composition according to the invention in a content ranging from 0.2% to 30% by weight, preferably in a content ranging from 0.5% to 15% by weight and better still from 1% to 10% by weight, relative to the total weight of the composition.

Alkylpolyglucoside Surfactants:

The dye composition according to the present invention also comprises one or more nonionic surfactants of alkylpolyglucoside type (iii).

The surfactants of alkylpolyglucoside type present in the cosmetic composition according to the present invention are more particularly represented by the general formula (II) below:

in which $R_1$ denotes a linear or branched alkyl and/or alkenyl radical comprising from about 8 to 24 carbon atoms, an alkylphenyl radical in which the linear or branched alkyl group comprises from about 8 to 24 carbon atoms, $R_2$ denotes an alkylene radical comprising from 2 to 4 carbon atoms, L denotes an optionally reduced sugar unit comprising from 5 to 6 carbon atoms, a denotes a value ranging from 0 to 10, preferably from 0 to 4, and b denotes a value ranging from 1 to 15.

Alkylpolyglucosides that are preferred according to the present invention are compounds of formula (II) in which $R_1$ more particularly denotes a linear or branched alkyl and/or alkenyl radical comprising from 9 to 14 carbon atoms and better still from 8 to 18 carbon atoms, a denotes a value ranging from 0 to 3 and even more particularly equal to zero and L denotes glucose, fructose or galactose. The degree of polymerization (S) of the saccharide, i.e. the value of b in formula (II), may range from 1 to 15 and preferably from 1 to 4. According to the invention, preference is given to optionally reduced sugars containing 80%, or more, of sugars whose degree of polymerization (S) takes a value ranging from 1 to 4.

The average degree of polymerization more particularly ranges from 1 to 2 and even more preferentially from 1.1 to 1.5.

The glycoside bonds between the sugar units are preferably of 1-6 or 1-4 type and even more preferentially of 1-4 type.

Compounds of formula (II) are especially represented by the products sold by the company Henkel under the name APG, such as the products APG 300, APG 350, APG 500, APG 550, APG 625 and APG Base 10-12; the products sold by the company SEPPIC under the names Triton CG 110 (or Oramix CG 110) and Triton CG 312 (or Oramix NS 10); those sold by the company BASF under the name Lutensol GD 70; sold by the company Henkel under the names Plantaren 1200, Plantaren 1300 and Plantaren 2000 and Plantacare 2000, Plantacare 818 and Plantacare 1200.

The nonionic surfactants of alkylpolyglucoside type (iii) may be present in the dye composition in a content ranging from 0.5% to 30% by weight, preferably in a content ranging from 1% to 15% by weight and better still from 1% to 5% by weight, relative to the total weight, of the composition.

Direct Dyes:

As indicated previously, the dye composition according to the invention comprises one or more direct dyes (v).

For the purposes of the present invention, the term "direct dye" means synthetic direct dyes and natural dyes, or mixtures thereof.

In particular, these hair dyes may be nonionic or ionic, in particular cationic or anionic.

The term "natural dye" means any dye or dye precursor that is naturally occurring and that is produced either by extraction (and possible purification) from a plant matrix, or via chemical synthesis.

In contrast, the term "synthetic dyes" means any dye that is not naturally occurring.

Examples of suitable synthetic direct dyes that may be mentioned include the following direct dyes: azos; methines; carbonyls; azines; nitro(hetero)aryls; tri(hetero)arylmethanes; alone or as mixtures.

More particularly, the azo dyes comprise an —N═N— function, the two nitrogen atoms of which are not simultaneously participants in a ring. However, it is not excluded for one of the two nitrogen atoms of the sequence —N═N— to be a participant in a ring.

The dyes of the methine family are more particularly compounds comprising at least one sequence chosen from >C═C< and —N═C< in which the two atoms do not simultaneously participate in a ring. However, it is pointed out that one of the nitrogen or carbon atoms of the sequences may be engaged in a ring. More particularly, the dyes of this family are derived from compounds of true methine type (comprising one or more abovementioned sequences —C═C—); of azomethine type (comprising at least one, or more, sequences —C═N—) with, for example, azacarbocyanines and isomers thereof, diazacarbocyanines and isomers thereof, and tetraazacarbocyanines; of mono- and diarylmethane type; of indoamine (or diphenylamine) type; of indophenol type; or of indoaniline type.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the azine family, mention may be made especially of azine, xanthene, thioxanthene, fluorindine, acridine, (di)oxazine, (di)thiazine and pyronin dyes.

The nitro(hetero)aromatic dyes are more particularly nitrobenzene or nitropyridine direct dyes.

As regards the dyes of porphyrin or phthalocyanine type, it is possible to use cationic or non-cationic compounds, optionally comprising one or more metals or metal ions, for instance alkali metals, alkaline-earth metals, zinc and silicon.

As examples of direct dyes that are particularly suitable for use, mention may be made of azo direct dyes; (poly)methine direct dyes, such as cyanines, hemicyanines and styryl dyes; azomethine direct dyes more particularly with diazacarbocyanines and isomers thereof and tetraazacarbocyanines (tetraazapentamethines); carbonyl direct dyes, for instance quinone direct dyes and in particular anthraquinones, naphthoquinones or benzoquinones; azine direct dyes; xanthene direct dyes; tri(hetero)arylmethane direct dyes; indoamine direct dyes; phthalocyanine and porphyrin direct dyes; nitro(hetero)aryl direct dyes and natural direct dyes, alone or as mixtures.

Preferably, the direct dyes are chosen from nitro(hetero)aryl direct dyes; azo direct dyes; azomethine direct dyes with diazacarbocyanines and isomers thereof; methine direct dyes, such as cyanines, hemicyanines and styryl dyes; anthraquinone direct dyes; xanthene direct dyes; tri(hetero)arylmethane direct dyes; alone or as mixtures.

Even more preferably, these direct dyes are chosen from nitro dyes of the benzene series; azo direct dyes; azomethine direct dyes, with diazacarbocyanines and isomers thereof, methine direct dyes, such as cyanines, hemicyanines and styryl dyes; xanthene direct dyes; alone or as a mixture.

Among the nitrobenzene direct dyes that may be used according to the invention, mention may be made in a non-limiting manner of the following compounds:
1,4-diamino-2-nitrobenzene
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β γ-dihydroxypropyloxy-3-methylamino-4-nitrobenzene
1-β-hydroxyethylamino-4-β,γ-dihydroxypropyloxy-2-nitrobenzene
1-β γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-(β-bisphydroxyethyl)amino-3-nitrobenzene
1-β-hydroxyethylamino-2-nitrobenzene
1-hydroxy-4-β-hydroxyethylamino-3-nitrobenzene.

Among the azo, azomethine, and methine direct dyes that may be used according to the invention, mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

Thus, mention may be made very especially of the cationic direct dyes corresponding to the following formula:

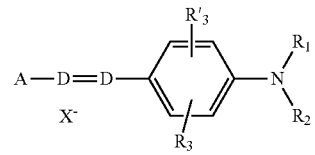

in which:
D represents a nitrogen atom or the —CH group,
$R_1$ and $R_2$, which may be identical or different, represent a hydrogen atom; a $C_1$-$C_4$ alkyl radical which is possibly substituted with a —CN, —OH or —NH$_2$ radical, or form, with a carbon atom of the benzene ring, an optionally oxygen-containing or nitrogen-containing heterocycle which may be substituted with one or more $C_1$-$C_4$ alkyl radicals; a 4'-aminophenyl radical,
$R_3$ and $R'_3$, which may be identical or different, represent a hydrogen atom or a halogen atom chosen from chlorine, bromine, iodine and fluorine, or a cyano, $C_1$-$C_4$ alkyl, $C_1$-$C_4$ alkoxy or acetyloxy radical,
$X^-$ represents an anion preferably chosen from chloride, methyl sulfate and acetate,
A represents a group chosen from the following structures:

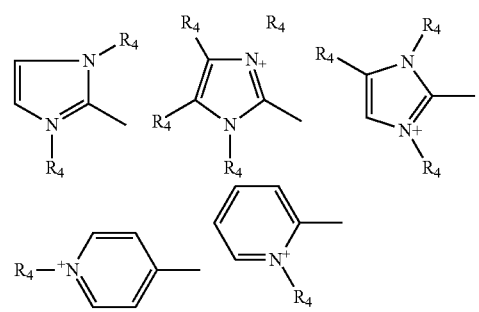

in which $R_4$ represents a $C_1$-$C_4$ alkyl radical which may be substituted with a hydroxyl radical;

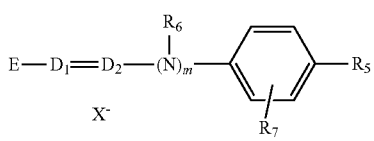

in which:

$R_5$ represents a hydrogen atom, a $C_1$-$C_4$ alkoxy radical or a halogen atom such as bromine, chlorine, iodine or fluorine, $R_6$ represents a hydrogen atom or a $C_1$-$C_4$ alkyl radical or forms, with a carbon atom of the benzene ring, a heterocycle which is optionally oxygen-containing and/or substituted with one or more $C_1$-$C_4$ alkyl groups, $R_7$ represents a hydrogen or halogen atom such as bromine, chlorine, iodine or fluorine, $D_1$ and $D_2$, which may be identical or different, represent a nitrogen atom or the —CH group, m=0 or 1, $X^-$ represents a cosmetically acceptable anion which is preferably chosen from chloride, methyl sulfate and acetate, E represents a group chosen from the following structures:

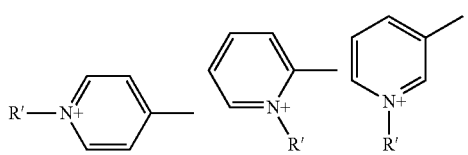

in which R' represents a $C_1$-$C_4$ alkyl radical;

when m=0 and when $D_1$ represents a nitrogen atom, E may then also denote a group of the following structure:

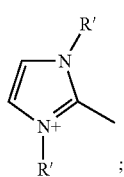

in which R' represents a $C_1$-$C_4$ alkyl radical.

Among the abovementioned compounds, use is made most particularly of the following compounds:

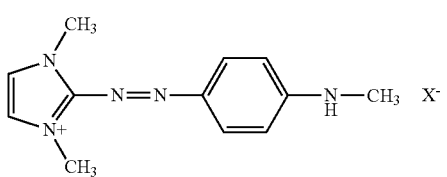

(A1)

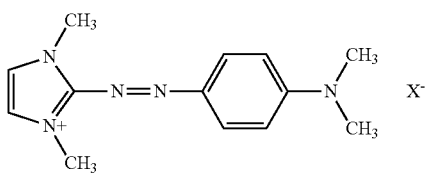

(A2)

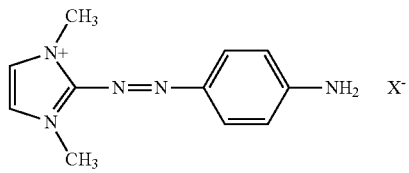

(A3)

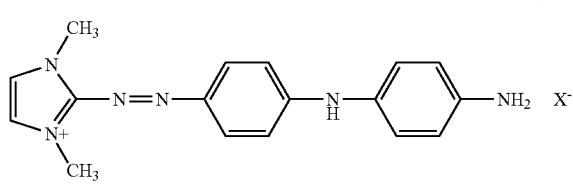

(A4)°

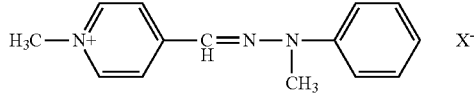

(A5)

(A6)

As other dyes that may be used according to the invention, mention may also be made, among the azo direct dyes, of the following dyes, which are described in the Colour Index International, 3rd edition: Disperse Red 17; Disperse Red 13; Basic Red 22; Basic Red 76; Basic Yellow 57; Basic Brown 16; Basic Brown 17; Disperse Green 9; Disperse Black 9; Solvent Black 3; Disperse Blue 148; Disperse Violet 63; Solvent Orange 7.

Mention may also be made of 1-(4'-aminodiphenylazo)-2-methyl-4-bis((3-hydroxyethyl)aminobenzene (INCI name: HC Yellow 7).

Among the quinone direct dyes that may be mentioned are the following dyes: Disperse Red 15; Solvent Violet 13; Solvent Blue 14; Disperse Violet 1; Disperse Violet 4; Disperse Blue 1; Disperse Violet 8; Disperse Blue 3; Disperse Red 11; Disperse Blue 7; Disperse Blue 14; Basic Blue 22; Disperse Violet 15; Disperse Blue 377; Disperse Blue 60; Basic Blue 99;

and also the following compounds:

1-N-methylmorpholiniumpropylamino-4-hydroxyanthraquinone 1-aminopropylamino-4-methylaminoanthraquinone 1-aminopropylaminoanthraquinone 5-β-hydroxyethyl-1,4-diaminoanthraquinone 2-aminoethylaminoanthraquinone 1,4-bis(β,γ-dihydroxypropylamino)anthraquinone.

Mention may also be made of the coumarin, Disperse Yellow 82.

Among the azine dyes, mention may be made of the following compounds: Basic Blue 17; Basic Red 2; Solvent Orange 15.

Among the triarylmethane dyes that may be used according to the invention, mention may be made of the following compounds: Basic Green 1; Basic Violet 3; Basic Violet 14; Basic Blue 7; Basic Blue 26.

Among the indoamine dyes that may be used according to the invention, mention may be made of the following compounds:

2-β-hydroxyethylamino-5-[bis(β-4'-hydroxyethyl)amino] anilino-1,4-benzoquinone

2-β-hydroxyethylamino-5-(2'-methoxy-4'-amino)anilino-1, 4-benzoquinone

3-N-(2'-chloro-4'-hydroxy)phenylacetylamino-6-methoxy-1,4-benzoquinone imine

3-N-(3'-chloro-4'-methylamino)phenylureido-6-methyl-1,4-benzoquinone imine

3-[4'-N-(ethyl,carbamylmethyl)amino]phenylureido-6-methyl-1,4-benzoquinone imine.

The cationic direct dyes are preferably chosen from direct dyes of the following types: azos, methines; azomethines with diazacarbocyanines and isomers thereof; xanthenes; anthraquinones; alone or as a mixture.

Among the anionic direct dyes, mention may be made in particular of those described in the COLOUR INDEX INTERNATIONAL 3rd edition under the name ACID, and in particular: Disperse Red 17; Acid Yellow 9; Acid Black 1; Acid Yellow 36; Acid Orange 7; Acid Red 33; Acid Red 35; Acid Red 52; Acid Yellow 23; Acid Orange 24; Acid Violet 43; Acid Blue 62; Acid blue 9; Acid Violet 49; Acid Blue 7.

The natural dye(s) that are in particular suitable for use in the invention are preferably chosen from lawsone, juglone, alizarin, purpurin, carminic acid, kermesic acid, laccaic acid, purpurogallin, anthragallol, protocatechaldehyde, indigo, isatin, curcumin, spinulosin, chlorophylls, chlorophyllines, orceins, haematein, brazileine, safflower dyes (for instance carthamine), flavonoids (with, for example, morin, apigenidin and sandalwood), anthocyans (such as apigeninidin), carotenoids, tannins, sorghum dyes and cochineal carmine, or mixtures thereof.

Extracts or decoctions containing these natural dyes, and in particular henna-based extracts, may also be used.

Preferably, the natural dye(s) are chosen from lawsone, juglone, alizarin, purpurin, carminic acid, kermesic acid, laccaic acid, purpurogallin, protocatechaldehyde, indigo, isatin, curcumin, spinulosin, apigenidin, chlorophylline, sorghum extracts, orceins, cochineal carmine, haematein and brazileine, and mixtures thereof.

These dyes may optionally be used in the presence of mordants (e.g. zinc, manganese, aluminium, iron, etc. salts).

The direct dyes (v) usually represent from 0.001% to 10% by weight, preferably from 0.01% to 8% by weight, and even more particularly from 0.1% to 5% by weight, relative to the weight of the composition.

It should be noted that since the composition concerns the direct dye, the latter does not comprise any oxidation dye precursors, which are compounds chosen from oxidation bases and couplers.

Examples of conventionally used oxidation bases that may be mentioned include para-phenylenediamines, bis(phenyl)alkylenediamines, para-aminophenols, ortho-aminophenols and heterocyclic bases, and the addition salts thereof.

Couplers that may especially be mentioned include meta-phenylenediamines, meta-aminophenols, meta-diphenols, naphthalene-based couplers and heterocyclic couplers, and also the addition salts thereof.

Basifying Agents:

When the composition according to the present invention contains one or more alkaline agents (iv), the alkaline agent may be organic or mineral or hybrid.

A first type of alkaline agents that may be used for the purposes of the present invention are organic amines with a $pK_b$ at 25° C. of less than 12, preferably less than 10 and even more advantageously less than 6. It should be noted that it is the $pK_b$ corresponding to the function of highest basicity.

According to a first variant of the invention, the organic amine comprises a primary, secondary or tertiary amine function and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for use in the invention.

Among compounds of this type, mention may be made of monoethanolamine, diethanolamine, triethanolamine, monoisopropanolamine, diisopropanolamine, N-dimethyl-aminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

Also suitable are the organic amines having the following formula:

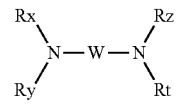

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

According to another variant of the invention, the organic amine is chosen from amino acids.

More particularly, the amino acids that may be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

Advantageously, the amino acids are basic amino acids comprising an additional amine function optionally included in a ring or in a ureido function.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

According to one preferred variant of the invention, the organic amine is chosen from basic amino acids. The amino acids that are particularly preferred are glycerine, tyrosine, arginine, lysine and histidine, or mixtures thereof.

According to another variant of the invention, the organic amine is chosen from organic amines of heterocyclic type. Besides histidine that has already been mentioned in the amino acids, mention may in particular be made of pyridine, piperidine, imidazole, triazole, tetrazole and benzimidazole.

According to another variant of the invention, the organic amine is chosen from amino acid dipeptides. As amino acid dipeptides that may be used in the present invention, mention may in particular be made of carnosine, anserine and balenine.

According to another variant of the invention, the organic amine is chosen from compounds comprising a guanidine function. As amines of this type that may be used in the present invention, besides arginine that has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Preferably, the organic amine is an alkanolamine. More preferentially, the organic amine is chosen from 2-amino-2-methyl-1-propanol and monoethanolamine, or mixtures thereof. Even more preferentially, the organic amine is monoethanolamine.

A second type of alkaline agent that may be used for the purposes of the present invention comprises organic or mineral salts (in this case they are referred to as hybrid alkaline agents) of the organic amines as described above.

Preferably, the organic salts are chosen from organic acid salts such as citrates, lactates, glycolates, gluconates, acetates, propionates, fumarates, oxalates and tartrates.

Preferably, mineral salts are chosen from hydrohalides (for example hydrochlorides), carbonates, hydrogen carbonates, sulfates, hydrogen phosphates and phosphates.

A third type of alkaline agent that may be used for the purposes of the present invention is mineral bases. Examples that may be mentioned include aqueous ammonia, carbonates such as sodium carbonate, potassium carbonate or ammonium carbonate, sodium hydroxide, potassium hydroxide, silicates, and metasilicates such as sodium metasilicate or potassium metasilicate, preferably carbonates and more preferentially an ammonium carbonate.

Preferably, the alkaline agents that may be used in the cosmetic composition according to the invention may be chosen from organic amines and salts thereof, organic bases and ammonium salts. In particular, the alkaline agent is monoethanolamine.

When the alkaline agents are present in the cosmetic composition in accordance with the present invention, these agents are present in a content ranging from 0.01% to 30% by weight and preferably from 0.1% to 20% by weight relative to the weight of the said composition.

Preferably, the composition of the invention comprises one or more alkaline agents.

Water/Solvents Other than Water:

The composition according to the invention preferably comprises water or a mixture of water and of one or more common water-soluble organic solvents.

For the purposes of the present invention, the term "water-soluble solvent" means a compound which is liquid at ordinary temperature (25° C.) and at atmospheric pressure ($1.013 \times 10^5$ Pa; 760 mmHg) with a solubility in water under these conditions of greater than or equal to 5%.

Preferably, the composition of the invention is aqueous, i.e. it contains water preferably in a content ranging from 5% to 50% by weight and better still from 5% to 30% by weight relative to the total weight of the dye composition.

The composition may comprise organic solvents. Among the suitable organic solvents, mention may be made more particularly of non-aromatic alcohols such as ethyl alcohol, isopropyl alcohol, or glycols or glycol ethers, for instance ethylene glycol monomethyl, monoethyl or monobutyl ether, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether, or alternatively polyols such as glycerol. Polyethylene glycols and polypropylene glycols, and mixtures of all these compounds, may also be used as solvent.

The common organic solvents described above, if they are present, usually represent from 0.1% to 15% by weight and more preferentially from 0.5% to 10% by weight relative to the total weight of the composition.

Additives:

Preferably, the cosmetic composition according to the present invention comprises one or more thickeners.

The thickeners may be chosen from mineral thickeners and organic thickeners.

The organic thickener(s) may be chosen from cellulose-based thickeners, for example hydroxyethylcellulose, hydroxypropylcellulose and carboxymethylcellulose, guar gum and derivatives thereof, for example the hydroxypropyl guar sold by the company Rhodia under the reference Jaguar HP 105, gums of microbial origin, such as xanthan gum and scleroglucan gum, synthetic thickeners such as crosslinked acrylic acid or acrylamidopropanesulfonic acid homopolymers, for example Carbomer, nonionic, anionic, cationic or amphoteric associative polymers, such as the polymers sold under the names Pemulen TR1 or TR2 by the company Goodrich, Salcare SC90 by the company Ciba, Aculyn 22, 28, 33, 44 or 46 by the company Rohm & Haas, and Elfacos T210 and T212 by the company Akzo.

According to one embodiment, the mineral thickeners are chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylaryl sulfonates and amine oxides, and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; quaternium-18/benzalkonium bentonites, such as those sold under the names Claytone HT and Claytone PS by Southern Clay; quaternium-18 hectorites, such as those sold under the names Bentone Gel DOA, Bentone Gel ECO5, Bentone Gel EUG, Bentone Gel IPP, Bentone Gel ISD, Bentone Gel SS71, Bentone Gel VS8 and Bentone Gel VS38 by Rheox, and Simagel M and Simagel SI 345 by Biophil.

The fumed silicas may be obtained by high-temperature hydrolysis of a volatile silicon compound in an oxyhydrogen flame, producing a finely divided silica. This process makes it possible especially to obtain hydrophilic silicas which contain a large number of silanol groups at their surface. Such hydrophilic silicas are sold, for example, under the names Aerosil 130®, Aerosil 200®, Aerosil 255®, Aerosil 300® and Aerosil 380® by Degussa and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of the silica by chemical reaction for the purpose of reducing the number of silanol groups. It is possible in particular to replace silanol groups with hydrophobic groups: a hydrophobic silica is then obtained.

The hydrophobic groups may be:
trimethylsiloxyl groups, which are obtained in particular by treating fumed silica in the presence of hexamethyldisilazane. Silicas thus treated are known as "Silica silylate" according to the CTFA (6th Edition, 1995) They are sold, for example, under the references Aerosil R812® by the company Degussa and Cab-O-Sil TS-530® by the company Cabot,
dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th Edition, 1995). They are sold, for example, under the references Aerosil R972® and Aerosil R974® by the company Degussa and Cab-O-Sil TS-610® and Cab-O-Sil TS-720® by the company Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

The composition according to the invention may also comprise various conventional adjuvants that are well known in the art, such as anionic, cationic, nonionic, amphoteric or zwitterionic polymers or mixtures thereof; antioxidants; penetrants; sequestrants; fragrances; dispersants; film-forming agents; ceramides; preserving agents; opacifiers, surfactants other than alkylpolyglucosides and in particular nonionic, anionic or amphoteric surfactants such as oxyethylenated fatty alcohols with an ethylene oxide number of greater than 10.

Those skilled in the art will take care to select the optional additives and the amount thereof such that they do not harm the properties of the compositions of the present invention.

These additives are generally present in the composition according to the invention in an amount ranging from 0 to 20% by weight relative to the total weight of the composition.

Generally, the pH of the cosmetic composition ranges from 2 to 12. The pH is adapted using acidifying or basifying agents.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

As regards the basifying agent, if it is present, it may be chosen from the alkaline agents described previously.

Processes:

In accordance with that which has been mentioned previously, the dye composition according to the present invention is used in a process for dyeing keratin fibres, in particular human keratin fibres such as the hair, under lightening or non-lightening conditions (with or without a chemical oxidizing agent).

According to a first embodiment of the invention, the process for dyeing keratin fibres, comprising the application to the said fibres of a dye composition as defined above, the composition preferably comprising one or more alkaline agents, is performed in the absence of an oxidizing composition comprising at least one chemical oxidizing agent.

In this case, the composition according to the invention may result from the extemporaneous mixing, before application to the fibres, of two compositions in which the direct dye(s) (v), the alkaline agent(s), if they are totally or partly in a composition other than that comprising the other obligatory components of the composition according to the invention, in other words the ingredients (i) to (iii) listed previously.

According to a second embodiment of the invention, the composition according to the invention is applied to the fibres in the presence of an oxidizing composition comprising one or more chemical oxidizing agents.

The oxidizing composition may be added to the composition of the invention directly onto the keratin fibres just before or after the application of the dye composition of the present invention.

Preferably, the oxidizing composition is added to the dye composition of the invention at the time of the use (application in the form of an extemporaneous mixture of the two compositions).

In this case also, the composition according to the invention free of chemical oxidizing agent may result from the extemporaneous mixing of two compositions in which the direct dye(s) (v), the alkaline agent(s) (iv), if they are present, are totally or partly in a composition other than that comprising the other obligatory components of the composition according to the invention, in other words the ingredients (i) to (iii) listed previously. These two compositions are then mixed with the oxidizing composition before application to the fibres.

According to the latter embodiment, the present invention more particularly relates to a process for dyeing keratin fibres, comprising the application to the said fibres of a composition according to the invention, this composition resulting from the mixing of three compositions, as defined below:
a composition (A) comprising at least one fatty substance (i), at least one oxyethylenated fatty alcohol with an oxyethylene number of less than or equal to 10 (ii), at least one nonionic surfactant of alkylpolyglucoside type (iii), optionally at least one direct dye (v), optionally at least one alkaline agent (iv),
a composition (B) comprising at least one direct dye (v) and/or at least one alkaline agent (iv),
the mixing of compositions (A) and (B) resulting in the dye composition according to the invention and preferably comprising at least one alkaline agent, in particular when the addition of a chemical oxidizing agent is envisaged in the process,
an oxidizing composition (C) comprising one or more chemical oxidizing agents.

Preferably, the dye composition (B) is an aqueous composition.

Even more preferentially, the water concentration may range from 10% to 90% by weight and better still from 20% to 80% of the total weight of the composition.

The pH of the dye composition (B), if it is aqueous, is between 2 and 12 and preferably between 8 and 11. The pH is adapted using acidifying or basifying agents such as those indicated previously.

Preferably, the dye composition (B) comprises one or more alkaline agents, as described previously. Preferably, the alkaline agent is present and is chosen from organic amines, especially alkanolamines, especially monoethanolamine.

As regards the oxidizing composition (C), it comprises as chemical oxidizing agent(s), which are other than atmospheric oxygen, compounds chosen from hydrogen peroxide, urea peroxide, alkali metal bromates or ferricyanides, peroxygenated salts, for instance alkali metal or alkaline-earth metal persulfates, perborates and percarbonates, and also peracids and precursors thereof.

Preferably, the chemical oxidizing agent(s) are chosen from hydrogen peroxide, urea peroxide and alkali metal bromates or ferricyanides.

This or these chemical oxidizing agent(s) are advantageously formed from hydrogen peroxide especially in aqueous solution (aqueous hydrogen peroxide solution), the concentration of which may range more particularly from 0.1% to 50% by weight, even more preferentially from 0.5% to 20% by weight and better still from 1% to 15% by weight relative to the weight of the oxidizing composition.

For the purpose of lightening and as a function of the desired degree of lightening, the hydrogen peroxide may be combined with one or more peroxygenated salts.

The oxidizing composition is in various forms, for instance a solution, an emulsion or a gel.

Compositions (B) and (C) may optionally comprise one or more conventional additives and solvents, such as those indicated previously.

According to a first variant of this second embodiment using the three abovementioned compositions, compositions (A), (B) and (C) are applied to wet or dry keratin fibres, successively and without intermediate rinsing, and more particularly compositions (A) and then (B) and then (C) or (B) and then (A) and then (C) are applied.

In accordance with a second variant of this second embodiment, the composition resulting from the mixing, prior to application, of compositions (A) and (B) and then the oxidizing composition (C) are applied to the keratin fibres, successively and without intermediate rinsing.

In accordance with a third variant of this embodiment, a composition obtained by extemporaneous mixing, before application, of compositions (A), (B) and (C) is applied to the wet or dry keratin fibres.

This third variant is preferred.

According to this variant, the final composition resulting from the mixing of (A), (B) and (C) preferably contains at least 20% by weight of fatty substance.

In this variant, the weight ratios R1 of the amounts of compositions (A)+(B)/(C) and R2 of the amounts of compositions (A)/(B) preferably range from 0.1 to 10 and preferably from 0.3 to 3.

Preferably, compositions (A), (B) and (C) are mixed before use.

Irrespective of the variant of the process used (with or without oxidizing agent, with one or more compositions premixed just before the application or applied successively without intermediate rinsing), the leave-on time on the fibres of the composition(s)/mixture(s) is from 3 to 50 minutes approximately and preferably 5 to 35 minutes approximately, the keratin fibres are rinsed, washed with shampoo, rinsed again and then dried.

The temperature during the process is conventionally between room temperature (between 15 and 25° C.) and 80° C. and preferably between room temperature and 60° C.

After the treatment, the human keratin fibres are optionally rinsed with water, optionally washed with a shampoo and then rinsed with water, before being dried or left to dry.

Devices:

The present invention also relates to a first multi-compartment device using a first compartment containing the aqueous cosmetic composition according to the invention and as defined above, a second compartment containing a cosmetic composition (C) comprising one or more chemical oxidizing agents.

According to another variant of the invention, the multi-compartment device comprises:
a first compartment containing a composition (A) comprising at least one fatty substance (i), at least one oxyethylenated fatty alcohol with an oxyethylene number of less than or equal to 10 (ii), at least one nonionic surfactant of alkylpolyglucoside type (iii), optionally at least one direct dye (v), optionally at least one alkaline agent (iv),
a second compartment containing a composition (B) containing at least one direct dye (v) and/or at least one alkaline agent (iv),
the mixing of the first and second compartments resulting in a dye composition according to the invention;
optionally a third compartment containing an oxidizing composition (C) comprising one or more chemical oxidizing agents.

The examples that follow serve to illustrate the invention without, however, being limiting in nature.

EXAMPLES

Example 1—Dyeing Under Non-Lightening Conditions

The following compositions are prepared, the contents being expressed, unless otherwise mentioned, in g % of active material:

Compositions A1 and A2

|  | A 1 (invention) | A 2 (prior art) |
| --- | --- | --- |
| Mineral oil | 80.5 | 0 |
| Laureth-2 | 1 | 1 |
| Cocoylglucoside | 3 | 3 |
| Water | 15.5 | 96 |

Composition B

|  | B |
| --- | --- |
| Acid Red 52 | 4.35 |
| Water | qs 100 |

At the time of the use, 12.5 g of compositions A1 or A2 are mixed with 2 g of composition B.

The pH of each mixture is adjusted to pH 7.5±0.2 by adding aqueous 20% citric acid solution.

Each mixture is then applied to a lock of Caucasian hair containing 100% white hairs (NG).

The "mixture/lock" bath ratio is 10/1 (w/w), respectively.

The leave-on time is 30 minutes at room temperature.

After this leave-on time, the locks are rinsed with tap water (flow rate: 300 L/h; temperature: 35° C.) for 10 seconds by passing the lock between the fingers (about 15 passes).

The locks are then drained between two fingers (about two passes) and then dried under a hood at 40° C.

The coloration obtained is measured using a Minolta CM2600D spectrocolorimeter.

The colour of the locks was evaluated in the CIE L* a* b* system, using a Minolta Spectrophotometer CM2600D colorimeter.

In this L* a* b* system, the three parameters denote, respectively, the colour intensity (L*), the green/red colour axis (a*) and the blue/yellow colour axis (b*).

The variation in coloration between the locks of grey hair containing 90% natural white hairs (90 NG) that are untreated (control) and after treatment or dyeing are defined by (ΔE*) according to the following equation:

$$\Delta E^* = \sqrt{(L^* - L_o^*)^2 + (a^* - a_o^*)^2 + (b^* - b_o^*)^2}$$

In this equation, $L^*$, $a^*$ and $b^*$ represent the values measured on locks of hair after dyeing and $L_o^*$, $a_o^*$ and $b_o^*$ represent the values measured on locks of undyed untreated hair. The higher the value of $\Delta E^*$, the better the colour build-up.

|  | L* (D65) | a* (D65) | b* (D65) | ΔE* (D65) |
|---|---|---|---|---|
| Untreated natural hair (NG) | 73.65 | 2.31 | 21.95 | — |
| NG treated with A1 + B (invention) | 52.5 | 35.71 | −2.08 | 46.26 |
| NG treated with A2 + B (prior art) | 58.66 | 29.13 | 4.33 | 35.42 |

As seen in the above table, composition A1 of the invention affords better coloration than the prior art composition A2.

Example 2—Dyeing Under Lightening Conditions

The following compositions are prepared (contents expressed in grams unless otherwise mentioned):

Compositions A1 and A2

|  | A 1 (invention) | A 2 (prior art) |
|---|---|---|
| Mineral oil | 80.5 | 0 |
| Laureth-2 | 1 | 1 |
| Cocoylglucoside | 3 | 3 |
| Water | 15.5 | 96 |

Composition C

|  | B |
|---|---|
| Acid Red 52 | 4.35 |
| Monoethanolamine | 14.5 |
| Water | qs 100 |

Oxidizing Composition D

|  | D |
|---|---|
| Hydrogen peroxide (50%) | 12 |
| Liquid petroleum jelly | 20 |
| Cetylstearyl alcohol | 8 |
| Oxyethylenated cetylstearyl alcohol (33 OE) | 3 |
| Tetrasodium pyrophosphate, 10 $H_2O$ | 0.03 |
| Disodium tin hexahydroxide | 0.04 |
| Polydimethyldiallylammonium chloride (non-stabilized, at 40% in water) | 0.5 |
| Poly[(dimethyliminio)-1,3-propanediyl(dimethyliminio)-1,6-hexanediyl dichloride] (aqueous 60% solution) | 0.25 |
| Protected oxyethylenated rapeseed acid amide (4 OE) | 1.3 |
| Antioxidant | 0.1 |
| Glycerol | 0.5 |
| Sequestrant | 0.06 |
| Phosphoric acid | qs pH 2.2 |
| Water | qs 100% |

At the time of use, 5 g of composition A1 or A2 are mixed with 2 g of composition C and 7.5 g of composition D.

The mixture pH values are 10.1±0.1.

Each mixture is then applied to a lock of Caucasian hair containing 100% white hairs (NG).

The "mixture/lock" bath ratio is 10/1 (w/w), respectively.

The leave-on time is 30 minutes at room temperature.

After this leave-on time, the locks are rinsed with tap water (flow rate: 300 L/h; temperature: 35° C.) for 10 seconds by passing the lock between the fingers (about 15 passes).

The locks are then drained between two fingers (about two passes) and then dried under a hood at 40° C.

The coloration obtained is measured using a Minolta CM2600D spectrocolorimeter.

As seen in the table below, composition A1 of the invention affords better coloration of the locks than the prior art composition A2.

|  | L* (D65) | a* (D65) | b* (D65) | E*ab (D65) |
|---|---|---|---|---|
| Untreated natural hair (NG) | 73.65 | 2.31 | 21.95 | — |
| NG treated with A1 + C + D (invention) | 65.46 | 30.01 | 7.4 | 32.34 |
| NG treated with A2 + C + D (prior art) | 67.54 | 23.07 | 11.27 | 24.13 |

The invention claimed is:

1. A composition for dyeing keratin fibers, comprising: composition (A) comprising:
   (i) at least one fatty substance present in an amount ranging from about 40% to about 85% by weight, relative to the total weight of the composition,
   (ii) at least one oxyethylenated fatty alcohol with an oxyethylene number less than or equal to 10,
   (iii) at least one nonionic surfactant of alkylpolyglucoside type,
   (iv) optionally at least one alkaline agent, and
   (v) optionally at least one direct dye chosen from cationic or anionic direct dyes;
   composition (B) comprising:
   (i) at least one direct dye chosen from cationic or anionic direct dyes, and/or
   (ii) at least one alkaline agent; and
   composition (C) comprising at least one chemical oxidizing agent,
   wherein the weight ratio $R_1$ of the amounts of composition (A)+(B)/(C) and $R_2$ of the amounts of compositions (A)/(B) ranges from 0.1 to 10.

2. The composition according to claim 1, wherein the at least one fatty substance is chosen from $C_6$-$C_{16}$ alkanes, hydrocarbons containing more than 16 carbon atoms, non-silicone oils of animal origin, plant oils of triglyceride type, synthetic triglycerides, fluoro oils, fatty alcohols, fatty acid and/or fatty alcohol esters other than triglycerides, plant waxes, non-silicone waxes, silicones, or mixtures thereof.

3. The composition according to claim 1, wherein the at least one fatty substance is chosen from liquid petroleum jelly, polydecenes, liquid fatty acid or fatty alcohol esters, liquid fatty alcohols, or mixtures thereof.

4. The composition according to claim 1, wherein the at least one oxyethylenated fatty alcohol has the following structure:

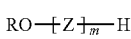

wherein:
R is a saturated or unsaturated, linear or branched radical comprising from 6 to 40 carbon atoms,
Z is an oxyethylene radical chosen from compounds of formula (I):

(I)

and
m represents the number of ethylene oxide groups less than or equal to 10.

5. The composition according to claim 1, wherein the at least one oxyethylenated fatty alcohol is chosen from saturated or unsaturated linear fatty alcohols comprising from 10 to 20 carbon atoms and from 2 to 8 ethylene oxide groups.

6. The composition according to claim 1, wherein the at least one oxyethylenated fatty alcohol is present in an amount ranging from about 0.2% to about 30% by weight, relative to the total weight of the composition.

7. The composition according to claim 1, in which the at least one nonionic surfactant of alkylpolyglucoside type is chosen from compounds of formula (II):

(II)

wherein:
$R^1$ is a linear or branched alkyl and/or alkenyl radical comprising from 8 to 24 carbon atoms, or an alkylphenyl radical in which the linear or branched alkyl group comprises from 8 to 24 carbon atoms,
$R^2$ is an alkylene radical comprising from 2 to 4 carbon atoms,
L is an optionally-reduced sugar unit comprising from 5 to 6 carbon atoms,
a is an integer ranging from 0 to 10, and
b is an integer ranging from 1 to 15.

8. The composition according to claim 7, in which the at least one nonionic surfactant of alkylpolyglucoside type is chosen from compounds of formula (II) wherein
$R^1$ is a linear or branched alkyl and/or alkenyl radical comprising from 9 to 14 carbon atoms,
a is an integer ranging from 0 to 3, and
L is chosen from glucose, fructose, or galactose.

9. The composition according to claim 1, wherein the at least one nonionic surfactant of alkylpolyglucoside type is present in an amount ranging from about 0.5% to about 30% by weight, relative to the total weight of the composition.

10. The composition according to claim 1, furthering comprising water or a water mixture, wherein the water mixture comprises water and at least water-soluble organic solvent.

11. The composition according to claim 10, wherein the water or water mixture is present in an amount ranging from about 5% to about 50% by weight, relative to the total weight of the composition.

12. The composition according to claim 1 comprising at least one alkaline agent chosen from organic amines or ammonium salts.

13. A process for dyeing keratin fibers, comprising:
(a) preparing a dye composition by mixing a composition (A), composition (B), and composition (C):
composition (A) comprising:
(i) at least one fatty substance present in an amount ranging from about 40% to about 85% by weight, relative to the total weight of the composition,
(ii) at least one oxyethylenated fatty alcohols with an oxyethylene number less than or equal to 10,
(iii) at least one nonionic surfactant of alkylpolyglucoside type,
(iv) optionally at least one alkaline agents, and
(v) optionally at least one direct dye chosen from cationic or anionic direct dyes;
composition (B) comprising:
(i) at least one direct dye chosen from cationic or anionic direct dyes, and/or
(ii) at least one alkaline agent; and
composition (C) comprising at least one chemical oxidizing agent,
wherein the weight ratio $R_1$ of the amounts of composition (A)+(B)/(C) and $R_2$ of the amounts of compositions (A)/(B) ranges from 0.1 to 10; and
(b) applying said dye composition to said keratin fibers.

14. A device for mixing and using a composition for dyeing keratin fibers, comprising:
a first compartment containing a composition comprising at least one fatty substance present in an amount ranging from about 40% to about 85% by weight, relative to the total weight of the composition; at least one oxyethylenated fatty alcohol with an oxyethylene number less than or equal to 10; at least one nonionic surfactant of alkylpolyglucoside type; optionally at least one alkaline agent; and at least one direct dye; and
a second compartment containing an oxidizing composition comprising at least one chemical oxidizing agent.

15. A device for mixing and using a composition for dyeing keratin fibers, comprising:
a first compartment containing a composition (A) comprising at least one fatty substance present in an amount ranging from about 40% to about 85% by weight; at least one oxyethylenated fatty alcohol with an oxyethylene number of less than or equal to 10; at least one nonionic surfactant of alkylpolyglucoside type; optionally at least one direct dye; and optionally at least one alkaline agent,
a second compartment containing a composition (B) containing at least one direct dye and/or at least one alkaline agent, and
optionally, a third compartment containing an oxidizing composition (C) comprising one or more chemical oxidizing agents.

* * * * *